(12) United States Patent
Shah et al.

(10) Patent No.: US 7,976,497 B2
(45) Date of Patent: Jul. 12, 2011

(54) MULTI-LAYER FILM WELDED ARTICULATED BALLOON

(75) Inventors: Tilak M. Shah, Cary, NC (US); Christopher D. Strom, Cary, NC (US)

(73) Assignee: Polyzen Inc., Apex, NC (US)

( * ) Notice: Subject to any disclaimer, the term of this patent is extended or adjusted under 35 U.S.C. 154(b) by 0 days.

(21) Appl. No.: 12/237,897

(22) Filed: Sep. 25, 2008

(65) Prior Publication Data
US 2009/0082724 A1 Mar. 26, 2009
US 2010/0137797 A2 Jun. 3, 2010

Related U.S. Application Data

(60) Provisional application No. 60/974,884, filed on Sep. 25, 2007.

(51) Int. Cl.
*A61M 31/00* (2006.01)
*A61M 37/00* (2006.01)

(52) U.S. Cl. .................... 604/103.06; 604/96.01

(58) Field of Classification Search .......... 606/192, 606/194; 604/96.01, 101.02, 103, 103.01–103.08, 604/103.11–103.14
See application file for complete search history.

(56) References Cited

U.S. PATENT DOCUMENTS

| | | | |
|---|---|---|---|
| 4,043,345 A | 8/1977 | Kramann et al. | |
| 4,311,146 A | 1/1982 | Wonder | |
| 4,327,736 A | 5/1982 | Inoue | |
| 4,555,242 A | 11/1985 | Saudagar | |
| 4,650,463 A | 3/1987 | LeVeen et al. | |
| 4,784,133 A | 11/1988 | Mackin | |
| 4,994,033 A | 2/1991 | Shockey et al. | |
| 5,116,310 A | 5/1992 | Seder et al. | |
| 5,219,792 A | 6/1993 | Kim et al. | |
| 5,234,454 A | 8/1993 | Bangs | |
| 5,360,414 A | 11/1994 | Yarger | |
| 5,433,252 A | 7/1995 | Wolf et al. | |
| 5,512,051 A | 4/1996 | Wang et al. | |
| 5,527,280 A | 6/1996 | Goelz | |
| 5,545,122 A | 8/1996 | Spruill | |
| 5,545,220 A | 8/1996 | Andrews et al. | |
| 5,679,423 A | 10/1997 | Shah | |
| 5,704,913 A * | 1/1998 | Abele et al. | 604/101.02 |
| 5,716,329 A | 2/1998 | Dieter | |

(Continued)

FOREIGN PATENT DOCUMENTS

JP 51-090376 A 8/1976

(Continued)

OTHER PUBLICATIONS

Unpublished U.S. Appl. No. 11/933,018.

*Primary Examiner* — Christopher D Koharski
(74) *Attorney, Agent, or Firm* — Steven J. Hultquist; Hultquist IP; Richard T. Matthews

(57) ABSTRACT

A method of fabrication of a medical balloon, and a balloon device useful for various medical balloon procedures, such as gastrointestinal, vascular, reproductive system, urinary system and pulmonary applications. At least two layers of a thermoplastic film are sealed at their peripheral edges and heat sealed at one or more locations inside an area enclosed by the sealed edges at predetermined locations, in one implementation of the balloon device. Such configuration enables the balloon to articulate to a desired shape upon inflation, with the desired shape being selected to accommodate a specific medical application.

5 Claims, 5 Drawing Sheets

U.S. PATENT DOCUMENTS

| | | | |
|---|---|---|---|
| 5,743,852 A | 4/1998 | Johnson | |
| 5,782,800 A | 7/1998 | Yoon | |
| 5,833,915 A | 11/1998 | Shah | |
| 5,843,116 A * | 12/1998 | Crocker et al. | 606/192 |
| 5,865,729 A | 2/1999 | Meehan et al. | |
| 5,868,776 A | 2/1999 | Wright | |
| 5,879,499 A | 3/1999 | Corvi | |
| 5,924,456 A | 7/1999 | Simon | |
| 5,935,115 A | 8/1999 | Espina | |
| 5,951,514 A | 9/1999 | Sahota | |
| 5,996,639 A | 12/1999 | Gans et al. | |
| 6,022,313 A | 2/2000 | Ginn et al. | |
| 6,102,929 A | 8/2000 | Conway et al. | |
| 6,156,053 A | 12/2000 | Ghandi et al. | |
| 6,249,708 B1 | 6/2001 | Nelson et al. | |
| 6,291,543 B1 | 9/2001 | Shah | |
| 6,352,077 B1 | 3/2002 | Shah | |
| 6,460,541 B1 | 10/2002 | Shah et al. | |
| 6,478,789 B1 | 11/2002 | Spehalski et al. | |
| 6,520,977 B2 | 2/2003 | Piraka | |
| 6,663,646 B1 | 12/2003 | Shah | |
| 6,712,832 B2 * | 3/2004 | Shah | 606/192 |
| 6,733,512 B2 | 5/2004 | McGhan | |
| 6,746,465 B2 | 6/2004 | Diederich et al. | |
| 6,805,662 B2 | 10/2004 | Shah et al. | |
| 6,827,710 B1 | 12/2004 | Mooney et al. | |
| 6,875,193 B1 | 4/2005 | Bonnette et al. | |
| 6,981,980 B2 | 1/2006 | Sampson et al. | |
| 7,041,056 B2 | 5/2006 | Deslauriers et al. | |
| 7,112,186 B2 | 9/2006 | Shah | |
| 7,470,251 B2 | 12/2008 | Shah | |
| 2003/0028097 A1 | 2/2003 | D'Amico et al. | |
| 2003/0088209 A1 | 5/2003 | Chiu et al. | |
| 2005/0015047 A1 | 1/2005 | Shah | |
| 2005/0222329 A1 | 10/2005 | Shah | |
| 2006/0212064 A1 | 9/2006 | Shah | |
| 2007/0212559 A1 | 9/2007 | Shah | |
| 2007/0239110 A1 | 10/2007 | Shah | |
| 2007/0299463 A1 | 12/2007 | Shah | |
| 2008/0172080 A1 | 7/2008 | Isham | |
| 2008/0188802 A1 | 8/2008 | Shah | |
| 2008/0262449 A1 | 10/2008 | Shah | |
| 2008/0262450 A1 | 10/2008 | Shah | |

FOREIGN PATENT DOCUMENTS

| | | |
|---|---|---|
| JP | 51-100833 A | 9/1976 |
| JP | 51-101084 A | 9/1976 |
| JP | 10-127771 A | 5/1998 |

* cited by examiner

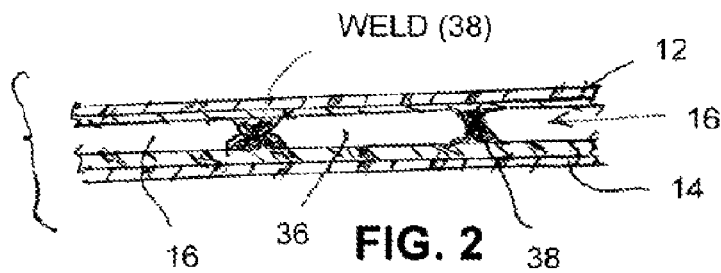
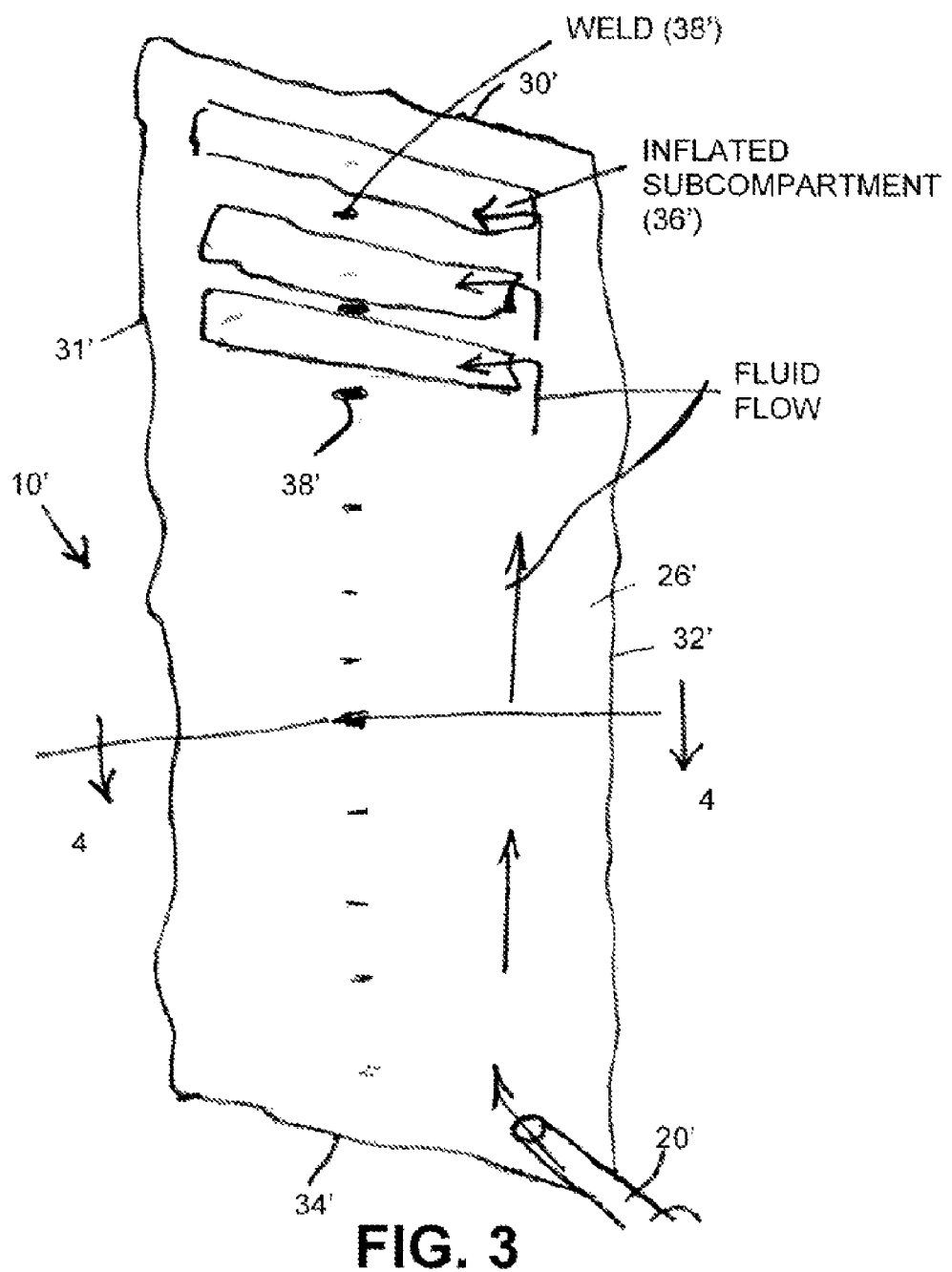

US 7,976,497 B2

MULTI-LAYER FILM WELDED ARTICULATED BALLOON

CROSS-REFERENCE TO RELATED APPLICATION

This application claims the benefit of priority under the provisions of 35 U.S.C. §119 of U.S. Provisional Patent Application No. 60/974,884 filed Sep. 25, 2007 in the name of Tilak M. Shah, et al. The disclosure of U.S. Provisional Patent Application No. 60/974,884 is hereby incorporated herein by reference, in its entirety for all purposes.

BACKGROUND OF THE INVENTION

1. Field of the Invention

The present invention relates to low pressure medical balloon articles and to the methodology for making the same, and in particular to a medical balloon useful for in vivo luminal medical procedures.

2. Description of the Prior Art

Various balloon articles are in use for cardiovascular and other medical procedures (such as percutaneous transluminal angioplasty, percutaneous transluminal nephrostomy, urethral dilatation, biliary duct dilatation, percutaneous transluminal renal angioplasty, and the like). Balloons may be utilized for such procedures, that are inflatable or otherwise capable of holding pressure. Pressure levels of balloons may be widely varied, depending on the specific application, and may for example be in a range of from 30-150 pounds per square inch (psi) for higher pressures and balloons and 1-10 psi for low pressure balloons.

Low pressure balloons are there which can hold a pressure on the order of 1-3 psi. Low pressure balloons are typically used for gastrointestinal applications. In other applications, balloons are employed in cardiovascular applications for blocking blood flow, or for removing/blocking a blood clot. In such applications, the balloon is typically bonded to the shaft of a catheter, and after inflation and use, the balloon is readily retracted to an original catheter sleeve shape.

An issue confronting the use of balloon articles for in vivo usage is the asymmetric character of the inflation.

There have been various attempts to shape the balloon so it can be articulated after inflation in vivo for its intended use. For example, in angioplasty applications, clots found in arteries should be held against the artery walls until treated or removed. In prostate treatments it is often desirable to space the prostate from the rectum while treating the same with radiation.

Usually, to achieve the desired inflated shape in low pressure balloons, the balloon material, often latex, is pre-stretched so as to achieve the desired final shape or the balloon has discrete portions which are overinflated so as to assume a desired shape after insertion and inflation. Another tactic employed is to precure particular selected balloon material so that when inflated, the balloon will assume the precured shape, or to form the balloon with a wall thickness which may vary at different locations in the balloon so as to expand at different rates to achieve different shaped portions in the balloon.

While the resultant balloon would be operational for its intended purpose, each requires an involved fabrication methodology.

SUMMARY OF THE INVENTION

The present invention relates to balloon articles useful in various medical procedures.

In one aspect, the present invention provides a method of fabrication of a medical balloon which uses at least two layers of a thermoplastic film sealed at their edges or periphery and heat sealed at one or more locations inside the area enclosed by the sealed edge at preselected locations, which enables the balloon to articulate to a desired shape upon inflation, with the specific shape being dependent on the particular medical application. The layers may have a different thickness or modulus of elasticity or any combination thereof or the same thickness and modulus, and different dimensioned channels formed by the heat sealed locations to articulate to a desired shape.

In a specific aspect, the invention relates to a method for the fabrication of an articulated medical balloon device comprising the steps of:

(a) providing at least two film layers having opposed edges;
(b) sealing said opposed edges to form a compartment adapted to receive fluid to expand said film layers relative to each other;
(c) providing an opening in said fluid compartment that is adapted to receive a lumen; and
(d) forming a subcompartment between the sealed edges of said compartment of a predetermined shape and dimension by sealing at least one of said layers to another, intermediate said opposed edges.

In a further aspect, the invention relates to a medical balloon device, comprising:

at least one film layer having an edge secured to a second film layer to form a fluid compartment therebetween, and portions of said film layers between said edges being secured intermediate said edges to form a plurality of subcompartments, and said fluid compartment being provided with an opening to receive a lumen.

Additional aspects, features and embodiments will be more fully apparent from the ensuing disclosure and appended claims.

BRIEF DESCRIPTION OF THE DRAWINGS

FIG. 2 is a cross-sectional view of the balloon of FIG. 1 taken substantially along the plane indicated by the line 2-2 of FIG. 1.

FIG. 3 is a top plan view of a second embodiment of the balloon of the present invention.

DETAILED DESCRIPTION OF THE PREFERRED EMBODIMENTS

Figure 1:
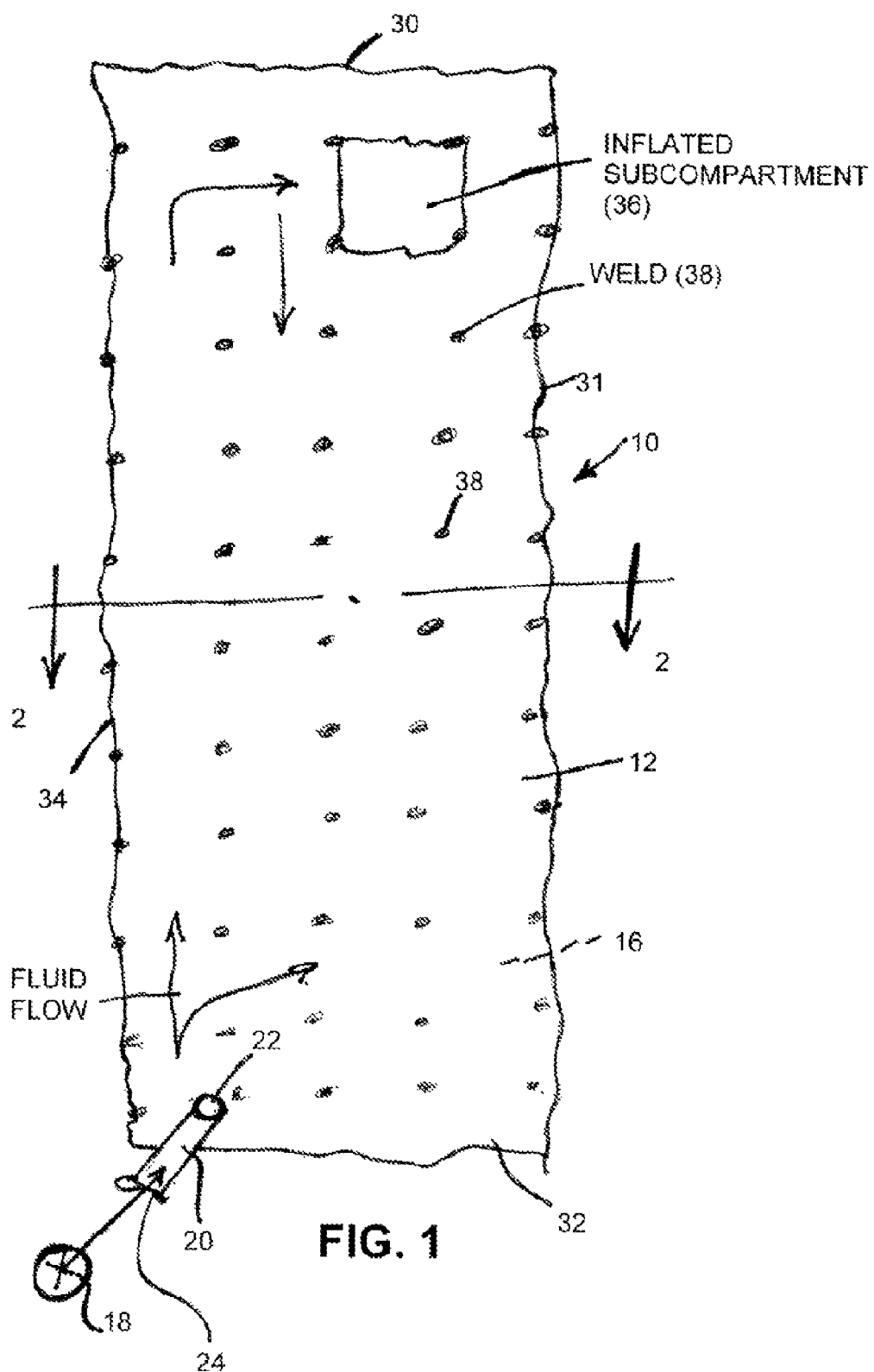
FIG. 1 is a top plan view of one embodiment of the balloon of the present invention.

Referring now to the drawings in detail, wherein like numerals indicate like elements throughout the several views, each of the inflatable balloon structures of the present invention, e.g., the balloon structure 10 of FIG. 1, comprises a multilayer arrangement of film layers 12, 14 or more, that includes an inflatable compartment 16 defining an enclosed interior volume and an anti-reflux valve 18 positioned in a lumen or fluid passage 20 whose distal end 22 is sealingly connected to the interior volume of compartment 16. An inflation bulb 24 is connected to the proximal end 24 of lumen 20 upstream from the anti-reflux valve 18. The valve 18 may be a one-way check valve or a rotatable stem in a housing having an opening adapted to be rotated into alignment with the bore of the lumen 20.

Oppositely facing film layers 26, 28 are bonded to one another along their edges 30-31, 32 and 34 to form the inflatable compartment 16 and the compartment 16 is divided into subcompartments 36 by tack or spot welds 38 so that the subcompartments 36 are virtually square-shaped in plan so that upon inflation, the balloon compartment 16 will resemble a tufted cushion with the tack or spot welds 38 forming raised square-shaped subcompartments. This device can be used to separate two organs in the body in vivo and support the same in spaced relation.

The inflatable balloon compartment and subcompartments can be readily formed by heat-sealing or other joining techniques commonly known and used in the art for forming structural articles from thermoplastic film materials in the form of web or sheet stock. For example, RF welding, heat impulse welding, solvent welding, adhesive bonding and the like can be employed.

Figure 4:
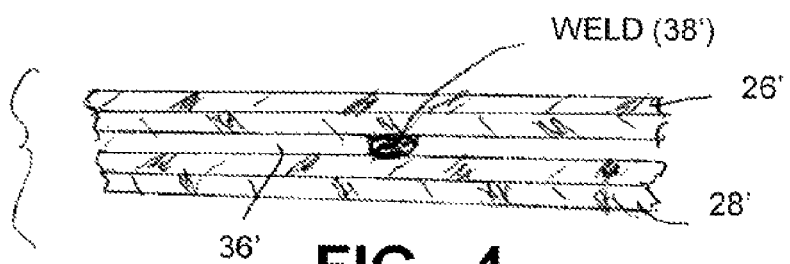
FIG. 4 is a cross-sectional view of the balloon of FIG. 3 taken substantially along the plane indicated by the line 4-4 of FIG. 3.
Figure 5:
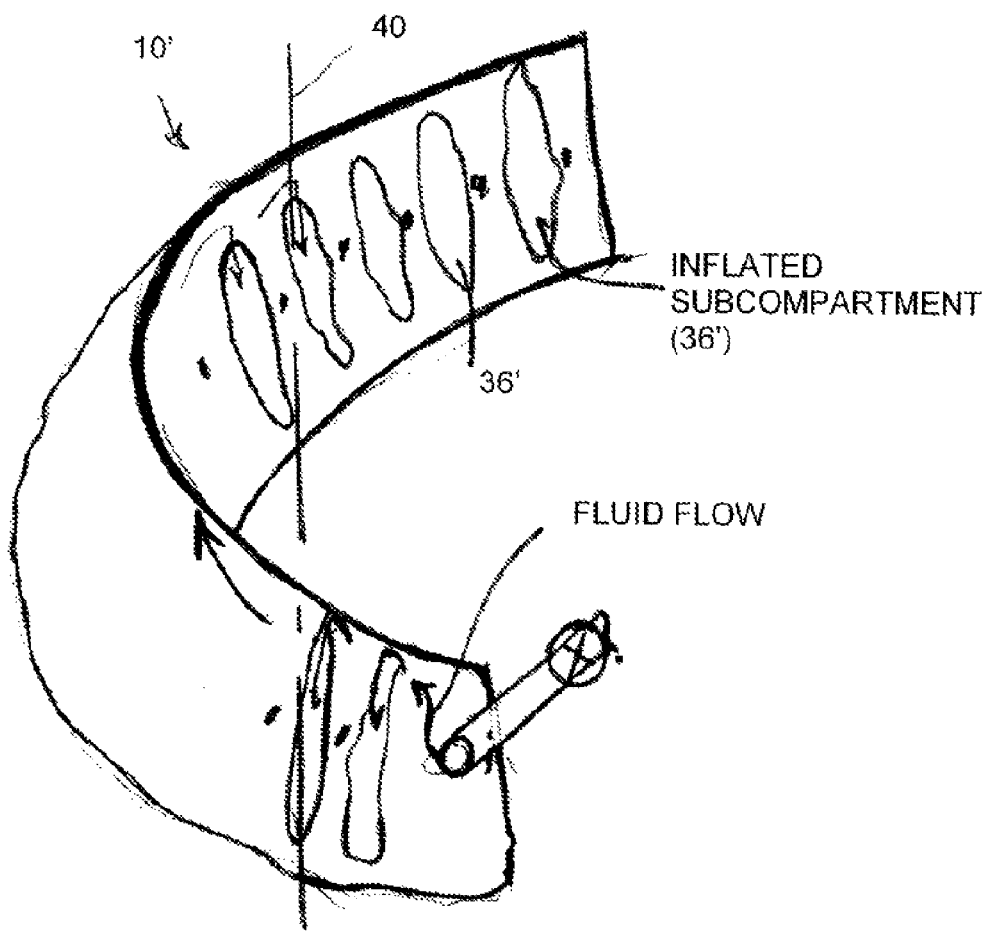
FIG. 5 is a perspective view of the articulated balloon of FIG. 3 after inflation.

Referring to the embodiment of the invention illustrated in FIGS. 3 to 5, inclusive, the film layers 26' and 28' may be bonded to each other in the shape of a parallelogram, with subcompartments 36' extending in spaced relation to each other, but parallel to the side edges 30' and 34' and at an angle to the opposite edges 31' and 32' by tack or spot welds 38'. As shown in FIG. 5, upon inflation, the fluid force introduced into the subcompartments 36' will cause the balloon device 10' to curl into a spiral about a longitudinal axis 40.

Figure 6:
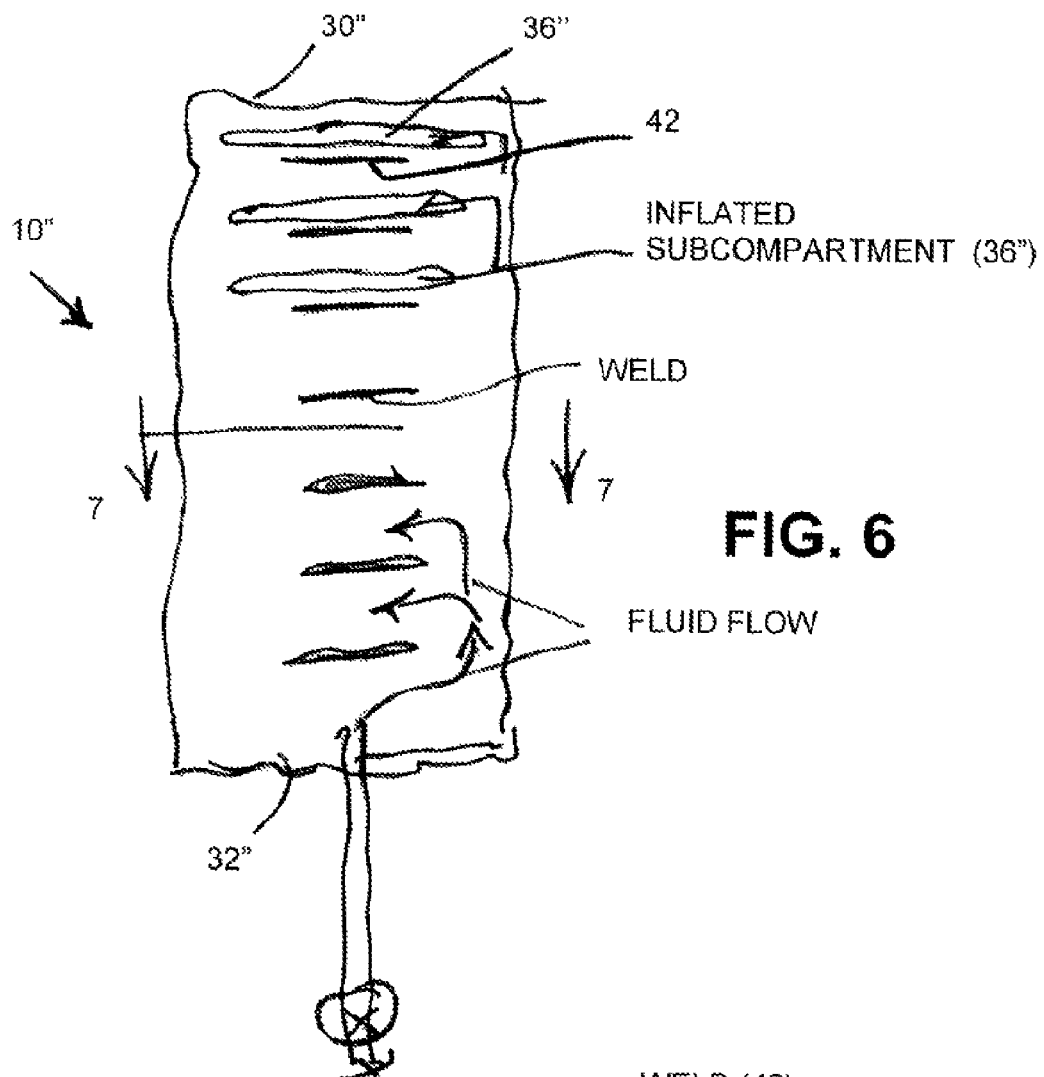
FIG. 6 is a top plan view of yet another embodiment of the balloon of the present invention.
Figure 7:
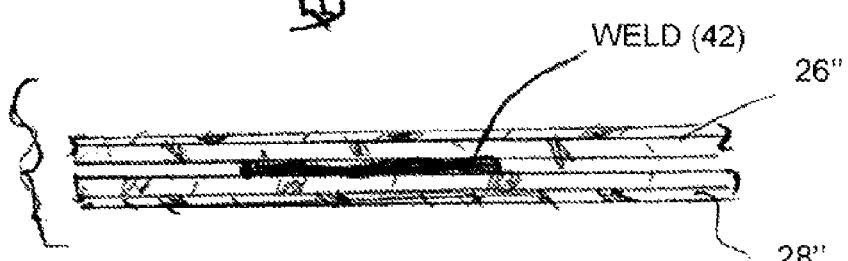
FIG. 7 is a cross-sectional view of the balloon of FIG. 6 taken substantially along the plane indicated by line 7-7 of FIG. 6.

Referring to FIGS. 6 and 7, the balloon device 10" can be formed with rectangular subcompartments 36" utilizing line welds 42, parallel to edges 30" and 32".

Figure 8:
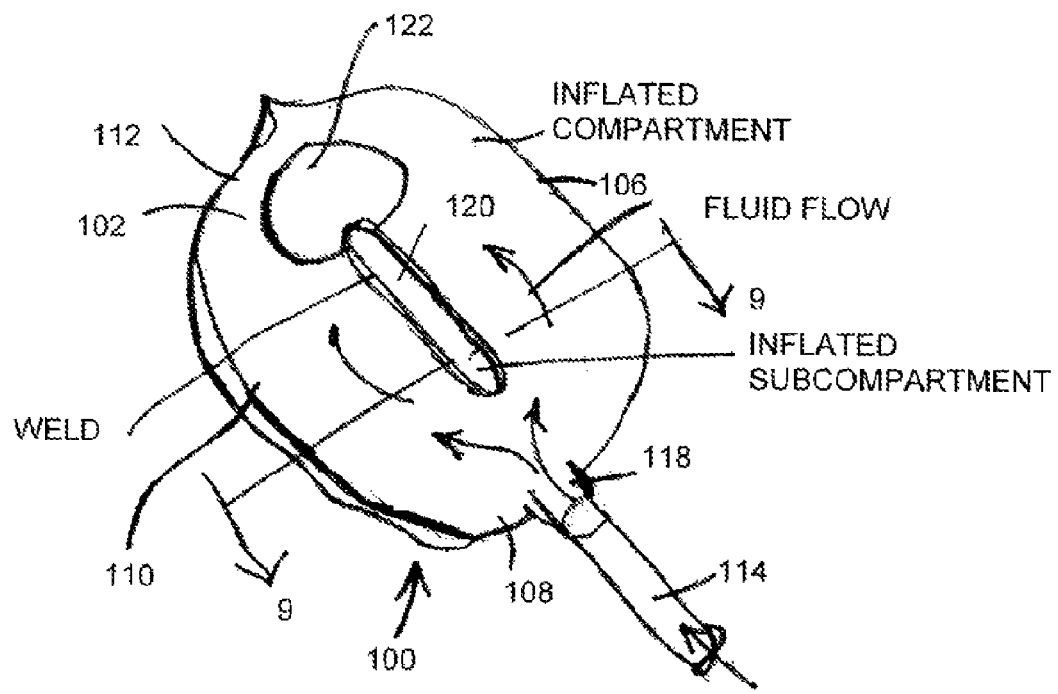
FIG. 8 is a perspective view of still another embodiment of an articulated balloon according to the present invention.
Figure 9:
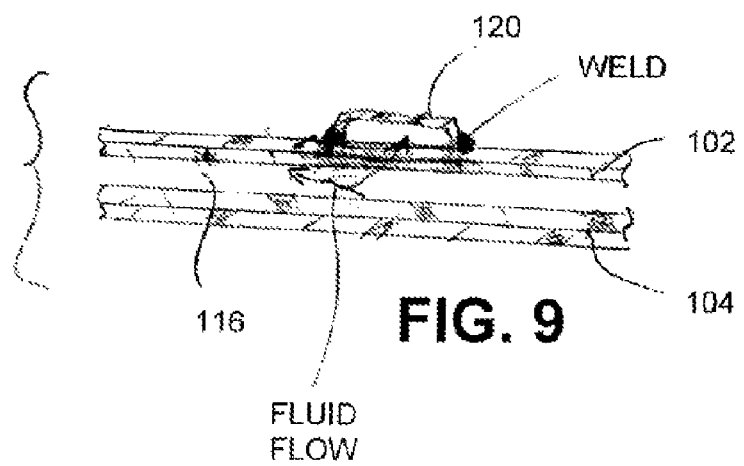
FIG. 9 is a cross-sectional view of the balloon of FIG. 8 taken substantially along the plane indicated by line 9-9 of FIG. 8.

As shown in the embodiment illustrated in FIGS. 8 and 9, the balloon device 100 has thermoplastic film layers 102 and 104 having different properties joined along their edges 106, 108, 110, and 112. For example, the materials can have a different modulus of elasticity, meaning that they will stretch under pressure at different rates to form a particular arcuate or curved shape. In this embodiment, the lumen 114 can extend into the interior of the compartment 116 formed by the film layers 102 and 104 and sealed to the balloon at neck 118.

Additionally, a third layer or strip of film 120 can be added or joined to the top layer 102 to increase its thickness. This will cause the sides 108, 112 to be drawn inwardly relative to the lumen axis, upon inflation, while the distal or forward portion of the compartment 122 will bulge upwardly. Such a device is useful in prostate surgery to support the prostate in spaced relation to other organs.

It will therefore be appreciated that the medical balloon device of the invention may be widely varied in construction and features. In one embodiment, the balloon device includes at least one neck member in a sealing area of the device. The device in a further embodiment comprises at least one area outside of the secured edges forming an inflation port.

While the invention has been illustratively shown and described with respective to particular embodiments, it will be appreciated that the application is not thus limited, but rather extends to and encompasses other variations, modifications and additional embodiments as will be apparent to those of ordinary skill in the art, based on the disclosure herein. Accordingly, the invention is intended to be broadly construed with respect to the ensuing claims, as encompassing all such additional variations, modifications and alternative embodiments.

What is claimed is:

1. A medical balloon device, comprising:
    a first thermoplastic film layer comprising a first material, wherein the first layer includes a first edge;
    a second thermoplastic film layer comprising a second material, wherein the second layer includes a second edge joined to the first edge to form a bottom inflatable compartment between the first and second layer;
    a third thermoplastic film layer including proximal and distal portions and comprising a third material different from the first and second materials wherein the third layer includes a third edge joined to the second edge to form a top inflatable compartment between the second and third layer; and
    an opening in said bottom inflatable compartment to receive a lumen, wherein the bottom inflatable compartment is in fluid communication with the top inflatable compartment.

2. The medical balloon device of claim 1, wherein the second and third layers are secured intermediate said second and third edges so that the distal portion of the third layer bulges upwardly upon inflation.

3. The medical balloon device of claim 1, wherein the top inflatable compartment is adapted to distend to form a bulged conformation of the distal portion of the third layer relative to the proximal portion upon inflation.

4. The medical balloon device of claim 1, wherein the top inflatable compartment is further secured between the second and third layers intermediate said second and third edges to form an arcuate shape in the distal portion of the third layer upon inflation.

5. The medical balloon device of claim 1, wherein the second and third layers are secured at an intermediate portion so that said third layer upon inflation bulges upwardly between the intermediate portion and the third edge at the distal portion of the third layer.

* * * * *

(12) EX PARTE REEXAMINATION CERTIFICATE (10272nd)
United States Patent
Shah et al.

(10) Number: US 7,976,497 C1
(45) Certificate Issued: Aug. 25, 2014

(54) MULTI-LAYERED FILM WELDED ARTICULATED BALLOON

(75) Inventors: Tilak M. Shah, Cary, NC (US); Christopher D. Strom, Cary, NC (US)

(73) Assignee: Polyzen Inc., Apex, NC (US)

Reexamination Request:
No. 90/013,179, Mar. 12, 2014

Reexamination Certificate for:
Patent No.: 7,976,497
Issued: Jul. 12, 2011
Appl. No.: 12/237,897
Filed: Sep. 25, 2008

Related U.S. Application Data

(60) Provisional application No. 60/974,884, filed on Sep. 25, 2007.

(51) Int. Cl.
*A61M 31/00* (2006.01)
*A61M 37/00* (2006.01)

(52) U.S. Cl.
USPC .................................. 604/103.06; 604/96.01

(58) Field of Classification Search
None
See application file for complete search history.

(56) References Cited

To view the complete listing of prior art documents cited during the proceeding for Reexamination Control Number 90/013,179, please refer to the USPTO's public Patent Application Information Retrieval (PAIR) system under the Display References tab.

*Primary Examiner* — William C. Doerrler

(57) ABSTRACT

A method of fabrication of a medical balloon, and a balloon device useful for various medical balloon procedures, such as gastrointestinal, vascular, reproductive system, urinary system and pulmonary applications. At least two layers of a thermoplastic film are sealed at their peripheral edges and heat sealed at one or more locations inside an area enclosed by the sealed edges at predetermined locations, in one implementation of the balloon device. Such configuration enables the balloon to articulate to a desired shape upon inflation, with the desired shape being selected to accommodate a specific medical application.

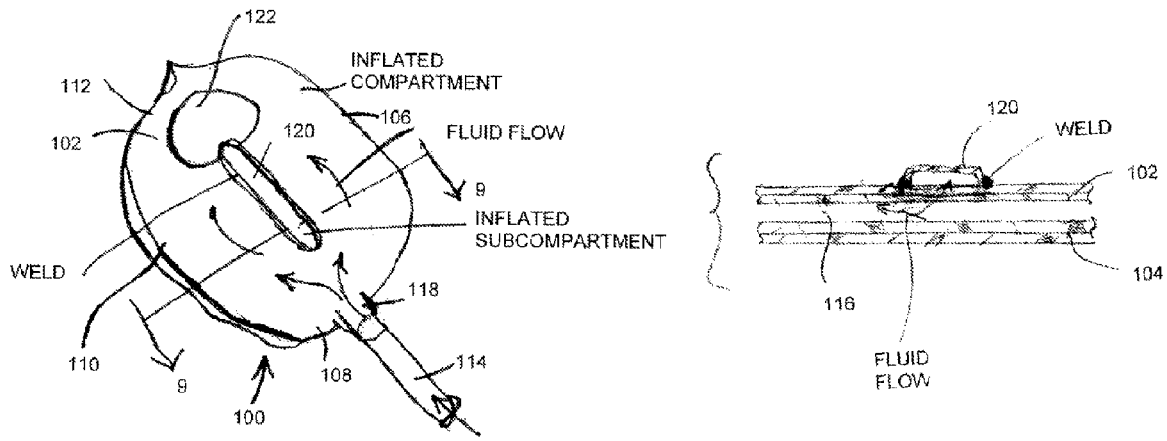

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claim 1 is confirmed.

Claims 2-5 were not reexamined.

\* \* \* \* \*